United States Patent [19]

Nadelson

[11] 4,011,340
[45] Mar. 8, 1977

[54] HYPOLIPIDEMIC BIS(PIVALOYLBENZYL) UREAS

[75] Inventor: Jeffrey Nadelson, Lake Parsippany, N.J.

[73] Assignee: Sandoz, Inc., E. Hanover, N.J.

[22] Filed: Oct. 28, 1975

[21] Appl. No.: 625,816

Related U.S. Application Data

[63] Continuation-in-part of Ser. No. 575,726, May 8, 1975, abandoned.

[52] U.S. Cl. .......................... 424/322; 260/553 A; 260/553 R; 260/570.8 R; 424/330
[51] Int. Cl.² ............... A61K 31/17; C07C 127/17
[58] Field of Search .................. 260/553 A, 553 R; 424/322

[56] References Cited
OTHER PUBLICATIONS

Houlihan et al., CA82:4001s (1975).
Houlihan et al., CA82:139642x (1975).

*Primary Examiner*—Daniel E. Wyman
*Assistant Examiner*—Thomas A. Waltz
*Attorney, Agent, or Firm*—Gerald D. Sharkin; Robert S. Honor; Timothy G. Rothwell

[57] ABSTRACT

Pivaloyl benzyl ureas, e.g., 1,1-bis(4-pivaloylbenzyl)-3-methyl urea, are prepared by reacting a corresponding 4'',4'''-iminodimethylene-di-tert. alkylophenones with an alkyl isocyanate, and are useful as hypolipidemic agents.

6 Claims, No Drawings

HYPOLIPIDEMIC BIS(PIVALOYLBENZYL) UREAS

This application is a continuation-in-part of application Ser. No. 575,726, filed May 8, 1975, now abandoned.

This invention relates to pivaloyl benzyl ureas which exhibit hypolipidemic activity. In particular, it relates to bis(p-pivaloylbenzyl)-3-substituted ureas and substituted or unsubstituted iminodimethylene-di-tert.-alkylophenones, to their preparation and intermediates thereof.

The compounds of this invention may be represented by the following structural formula:

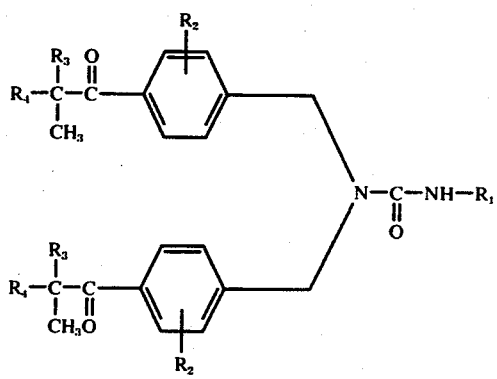

wherein
$R_1$ represents lower alkyl, i.e., alkyl having 1 to 4 carbon atoms, e.g., methyl, ethyl and the like, and
$R_2$ each independently represents hydrogen or halo having an atomic weight of about 19 to 36, i.e., fluoro or chloro, and
$R_3$ and $R_4$ each independently represent alkyl having 1 to 2 carbon atoms, i.e., methyl or ethyl.

The compounds of formula (I) are prepared according to the following reaction scheme:

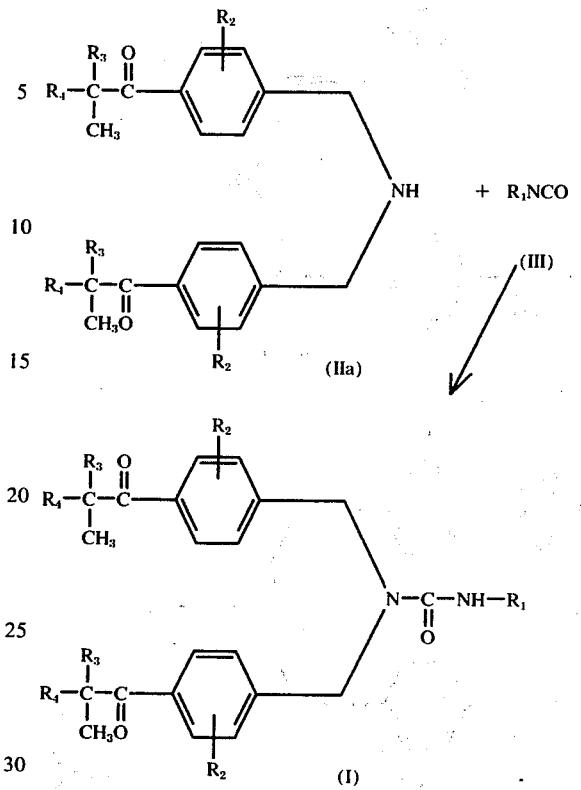

where $R_1$, $R_2$, $R_3$ and $R_4$ are as defined above.

The compounds of formula (I) are prepared by treating a compound of the formula (IIa) with a compound of the formula (III) in the presence of an inert organic solvent. Although the particular solvent employed is not critical, the preferred solvents include an aromatic hydrocarbon such as benzene, toluene and the like, or an ether such as diethylether, or tetrahydrofuran, the latter being especially preferred. The temperature of the reaction is not critical, but it is preferred that the reaction be run from about 0° to 100° C., preferably from about 20° to 30° C. The reaction is run from about 8 to 24 hours, preferably from about 15 to 20 hours. The product is recovered using conventional techniques, e.g., crystallization.

The compounds of formulae (IIa) and (IIb) are prepared according to the following reaction scheme:

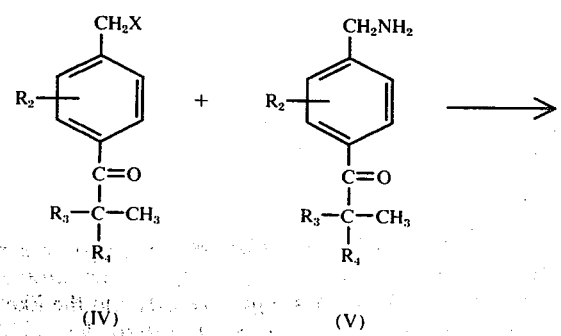

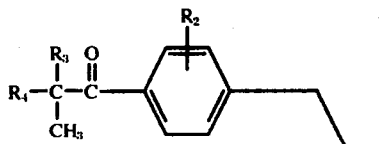

(IIa)

+

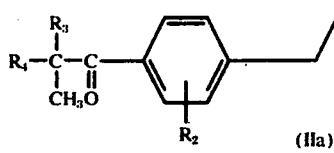

(IIb)

where
X is chlorine or bromine and
$R_2$, $R_3$ and $R_4$ are as defined above.

The compounds of formulae (IIa) and (IIb) are prepared by treating a compound of the formula (IV) with a compound of the formula (V) in the presence of an inert organic solvent. Furthermore, it is preferred that the reaction be carried out in the presence of an acid-binding agent, such as triethylamine, pyridine or N,N-diisopropylethylamine, the latter being especially preferred. Although the particular solvent employed is not critical, the preferred solvents include an aromatic hydrocarbon such as benzene, toluene, and the like or a halogenated hydrocarbon, such as methylenedichloride, chloroform and the like, preferably toluene. The temperature of the reaction is not critical, but it is preferred that the reaction be run from about 60° to 180° C., preferably the reflux temperature of the solvent. The reaction is run from about 8 to 24 hours, preferably from about 15 to 20 hours. The products are recovered using conventional techniques, e.g., trituration followed by filtration.

The compounds of formula (V) are prepared according to the following reaction scheme:

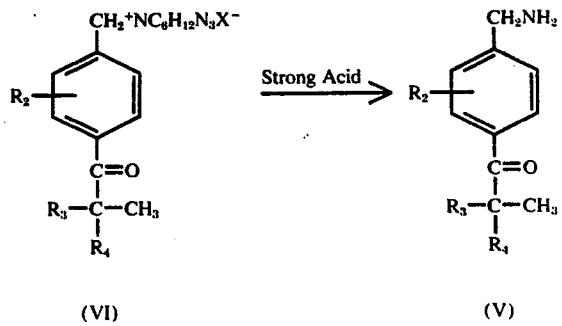

(VI)          (V)

where $R_2$, $R_3$, $R_4$ and X are as defined above.

The compounds of formula (V) are prepared by treating a compound of the formula (VI) with a strong acid such as hydrochloric, sulfuric, polyphosphoric or trichloroacetic acid in the presence of an aqueous solvent. Although the particular aqueous solvent used is not critical, it is preferred that the reaction be carried out in the presence of water only. The temperature of the reaction is not critical, but it is preferred that the reaction be run from about 80° to 120° C., especially at the reflux temperature of the solvent. The reaction is run for about 3 to 12 hours, preferably until no further formaldehyde is evolved. The product is recovered by conventional techniques, e.g., evaporation.

The compounds of formula (VI) are prepared according to the following reaction scheme:

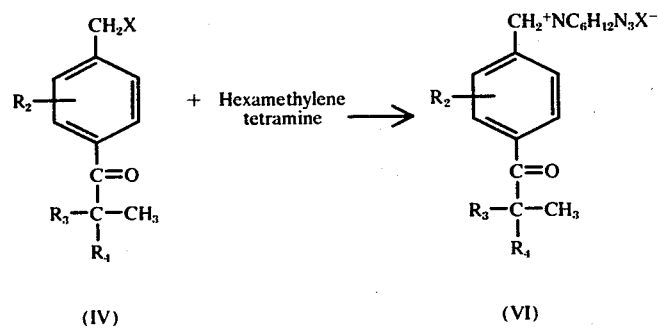

where $R_2$, $R_3$, $R_4$ and X are as defined above.

The compounds of formula (VI) are prepared by treating a compound of the formula (IV) with a compound of the formula (VII) in the presence of an inert organic solvent. Although the particular solvent employed is not critical, the preferred solvents include an aromatic hydrocarbon, such as benzene, toluene and the like, or a halogenated hydrocarbon such as methylenedichloride or chloroform, the latter being especially preferred. The temperature of the reaction is not critical, but it is preferred that the reaction be run from about 10° to 50° C., preferably from about 20° to 30° C. The reaction is run from about 24 to 72 hours, preferably from about 40 to 56 hours. The product is recovered using conventional techniques, e.g., filtration.

Many of the compounds of formulae (III) and (IV) are known and may be prepared by methods described in the literature. The compounds of formulae (III) and (IV) not specifically disclosed may be prepared by analogous methods from known starting materials.

The compounds of formulae (I), (IIa), (IIb) and (V) are useful because they possess pharmacological activity in animals as hypolipidemic agents, particularly as hyperlipoproteinemic agents as indicated by the fall in cholesterol and triglyceride levels in male albino Wistar rats weighing 110–130 g. initially. The rats are maintained on drug-free laboratory chow diet for 7 days and then divided into groups of 8 to 10 animals. Each group with the exception of the control is then given orally 120 milligrams per kilogram of body weight per diem of the compound for 6 days. At the end of this period, the animals are anesthetized with sodium hexobarbital and bled from the carotid arteries. Serum or plasma samples are collected, and 1.0 ml. samples of the serum are added to 9.0 ml. redistilled isopropanol. Two autoanalyzer cupsful of a mixture of zeolite-copper hydroxide and Lloydds reagent (Kessler, G., and Lederer, H., 1965, Technicon Symposium, Mediad Inc., New York, 345–347) are added, and the mixture is shaken for 1 hour. Cholesterol and triglyceride levels are determined simultaneously on the same sample by Technicon N 24 A (cholesterol) and N-78 (triglyceride) methodology. The mean total serum cholesterol levels are then computed and the hypocholesterolemic activity is expressed as the fall in cholesterol levels as a percentage of the control level. The change in serum triglyceride levels induced by the drug is computed as a percentage of the control triglyceride levels.

The compounds of formula (V) are also useful as anti-obesity agents, in the treatment of obesity as indicated by (1) preventing an increase in the blood sugar level in male Wistar rats in groups of four which have fasted for 16 hours and then are given an initial dose of 200 milligrams per kilogram of animal body weight of the test compound orally. One hour later, the rats are given 2 grams per kilogram of animal body weight of maltose load. Fifteen minutes after administration of the maltose, the rats are anesthetized with 120 milligrams per kilogram of animal body weight of sodium hexobarbital after which blood is collected via cardiac puncture. The blood samples are placed in an autoanalyzer cup containing 0.1 milliliters of heparin (1,000 units per milliliter). The heparinized blood is used to determine the blood sugar level with an autoanalyzer. The blood sugar content is compared to the control group which receives 0.5% carboxmethyl cellulose and are run concurrently, and by (2) preventing an increase in the blood sugar level in male Wistar rats in groups of four which are fasted for 16 hours and then are given an initial dose of 200 milligrams per kilogram of animal body weight of the test compound orally. One hour later, the rats are give 2.5 grams per kilogram of animal body weight of starch load. Thirty minutes after administration of the starch, the rats are anesthetized with 120 milligrams per kilogram of animal body weight of sodium hexobarbital after which blood is collected via cardiac puncture. The blood samples are placed in an autoanalyzer cup containing 0.1 milliliters of heparin (1,000 units per milliliter). The heparinized blood is used to determine the blood sugar level with an autoanalyzer. The blood sugar content is compared to the control group which receives 0.5% carboxmethyl cellulose and are run concurrently. The blood sugar levels are calculated and compared to the control.

For such usage, the compounds (I), (IIa), (IIb) and (V) may be combined with a pharmaceutically acceptable carrier or adjuvant and may be administered orally or parenterally as such or admixed with conventional pharmaceutical carriers. They may be administered in such forms as tablets, dispersible powders, granules, capsules, syrups, and elixirs and parenterally as solutions, suspensions, dispersions, emulsions and the like, e.g., a sterile injectable aqueous solution. The dosage will vary depending upon the mode of administration utilized and the particular compound employed.

The compounds of formulae (IIa), (IIb) and (V) may be similarly administered in the form of their non-toxic pharmaceutically acceptable salts. Such salts possess the same order of activity as the free base and are readily prepared by reacting the base with an appropriate acid by reacting the base with an appropriate acid by conventional techniques and, accordingly, are included within the scope of this invention. Representative of such salts are the mineral acid salts, e.g., hydrochloride, hydrobromide, sulfate and the like, and the organic acid salts such as succinate, benzoate, maleate and the like.

The hypolipidemic effective dosage of compounds (I), (IIa), (IIb) and (V) employed in the alleviation of lipidemia may vary depending on the particular compound employed and the severity of the condition being treated. However, in general, satisfactory results are obtained when the compounds of formulae (I), (IIa), (IIb) and (V) are administered at a daily dosage of from about 4.0 milligrams to about 250 milligrams per kilogram of animal body weight, preferably given in divided doses two to four times a day, or in sustained release form. For most large mammals, the total daily dosage is from about 300 milligrams to about 3000 milligrams. Dosage forms suitable for internal use comprise from about 75.0 to about 1500 milligrams of the active compound in intimate admixture with a solid or liquid pharmaceutically acceptable carrier or diluent.

The anti-obesity effective dosage of compounds (V) employed in the treatment of obesity may vary depending on the particular compound employed, the mode of administration and the severity of the condition being treated. However, in general satisfactory results are obtained when the compounds of formula (V) are administered at a daily dosage of from about 1 milligram to about 150 milligrams per kilogram of animal body weight, p.o., preferably given in divided doses two to four times a day, or in sustained release form. For most large mammals, the total daily dosage is from about 60 to about 1000 milligrams. Dosage forms suitable for internal use comprise from about 15 to about 500 milligrams of the active compound in intimate admixture with a solid or liquid pharmaceutically acceptable carrier or diluent.

A representative formulation suitable for oral administration two to four times a day for the treatment of lipidemia is a capsule prepared by standard encapsulating techniques which contains the following:

| Ingredients | Weight (mg.) |
|---|---|
| 1,1'-bis(p-pivaloylbenzyl)-3-methyl urea | 150 |
| inert solid diluent (starch, lactose, kaolin) | 300 |

EXAMPLE 1

4-Pivaloyl benzylamine hydrochloride

An ice solution of 127.5 g (0.5 mole) of α-bromo-4-pivaloyl toluene in 600 ml. of chloroform is added dropwise to 77.0 g (0.55 mole) of hexamethylene tetramine in 550 ml. chloroform. The resulting mixture is stirred for 2 days at room temperature and the solvent evaporated in vacuo. The residue is treated with ether and the resulting solid filtered and washed thoroughly with ether to give a white solid, 1-(4-pivaloylbenzyl)-3,5,7-triaza-1-azonia-adamantane bromide. The resulting solid is suspended in 300 ml. of 6N hydrochloric acid and steam distilled until no more formaldehyde is evolved. The distillation residue is poured onto ice and 180 ml. of 50% sodium hydroxide. The basic solution is extracted with ether and the ether is washed with water, brine and dried over anhydrous magnesium sulfate, filtered and evaporated in vacuo. The residue is dissolved in ethanol and treated with ether/hydrochloric acid to give 4-pivaloyl benzylamine hydrochloride, m.p. 222° C. to 225° C.

Following the above procedure and using in place of α-bromo-4-pivaloyl toluene, an equivalent amount of
  a. α-bromo-2-fluoro-4-pivaloyl toluene, or
  b. α-bromo-2-chloro-4-pivaloyl toluene,
there is obtained
  a. 2-fluoro-4-pivaloyl benzylamine hydrochloride, or
  b. 2-chloro-4-pivaloyl benzylamine hydrochloride, respectively.

The 4-pivaloyl benzylamine hydrochloride of this example is an effective anti-obesity agent when orally administered to an animal suffering from obesity at a dosage of 150 mg. four times per day.

EXAMPLE 2 a. 4'-[bis(4-pivaloylbenzyl)aminomethyl]-2,2-dimethylpropiophenone hydrochloride, and b. 4'',4'''-iminodimethylene-dipivalophenone hydrochloride A mixture of 15.1 g. (0.079 mole) of 4-pivaloyl benzylamine and 10.2 g. (0.079 mole) N,N-diisopropylethylamine in 170 ml. toluene maintained at room temperature is added dropwise to 20.2 g. (0.079 mole) of α-bromo-4-pivaloyl toluene in 200 ml. toluene. After addition is complete, the mixture is refluxed overnight, cooled and filtered. The solvents are evaporated in vacuo and the residue treated with ether and filtered. The ether filtrate is treated with 2N hydrochloric acid and the resulting solid washed with water and then ether. The solid is triturated with hot ethanol and filtered to give 4'[bis(4-pivaloylbenzyl)aminomethyl]-2,2-dimethylpropiophenone hydrochloride, m.p. 238° to 242° C. The ethanol filtrate is cooled and the solid filtered to give 4'',4'''-iminodimethylene-dipivalophenone hydrochloride, m.p. 233° to 236° C.

Following the above procedure and using in place of 4-pivaloyl benzylamine and α-bromo-4-pivaloyl toluene, an equivalent amount of
  a. α-bromo-2-fluoro-4-pivaloyl toluene and 2-fluoro-4-pivaloyl benzylamine, or
  b. α-bromo-2-chloro-4-pivaloyl toluene and 2-chloro-4-pivaloyl benzylamine,
there is obtained
  a. 4'-[bis(2-fluoro-4-pivaloylbenzyl)aminomethyl]-3'-fluoro-2,2-dimethylpropiophenone hydrochloride, or
  b. 4'-[bis(2-chloro-4-pivaloylbenzyl)aminomethyl]-3'-chloro-2,2-dimethylpropiophenone hydrochloride, respectively, and
  c. 3'',3'''-difluoro-4'',4'''-iminodimethylene-dipivalophenone hydrochloride, or
  d. 3'',3'''-dichloro-4'',4'''-iminodimethylene-dipivalophenone hydrochloride, respectively.

The 4'-[bis(4-pivaloylbenzyl)aminomethyl]-2,2-dimethylpropiophenone hydrochloride and the 4'',4'''-imino-dimethylene-dipivalophenone hydrochloride of this example are effective hypolipidemic agents when orally administered to an animal suffering from lipidemia at a dosage of 150 mg. four times per day.

EXAMPLE 3

1,1-Bis(4-pivaloylbenzyl)-3-methyl urea

A solution of 2.4 g (0.0065 mole) of 4'',4'''-iminodimethylene-dipivalophenone in 15 ml. tetrahydrofuran at room temperature is treated with 0.39 g. (0.0065 mole) methylisocyanate. The mixture is stirred at room temperature overnight and then the solvent is removed in vacuo. The residue is crystallized from ether/petroleum ether to give 1,1'-bis(4-pivaloylbenzyl)-3-methyl urea, m.p. 102° to 103° C.

Following the above procedure and using in place of 4'',4'''-iminodimethylene-dipivalophenone, an equivalent amount of a. 3'',3'''-difluoro-4'',4'''-iminodimethylene-dipivalophenone, or b. 3'',3'''-dichloro-4'',4'''-iminodimethylene-dipivalophenone, there is obtained a. 1,1-bis(2-fluoro-4-pivaloylbenzyl)-3-methyl urea, or b. 1,1-bis(2-chloro-4-pivaloylbenzyl)-3-methyl urea, respectively.

Again following the above procedure but using in place of methylisocyanate, an equivalent amount of ethylisocyanate, there is obtained 1,1-bis(4-pivaloylbenzyl)-3-ethyl urea.

The 1,1-bis(4-pivaloylbenzyl)-3-methyl urea of this example is an effective hypolipidemic agent when orally administered to an animal suffering from lipidemia at a dosage of 150 mg. four times per day.

What is claimed is:

1. A compound of the formula

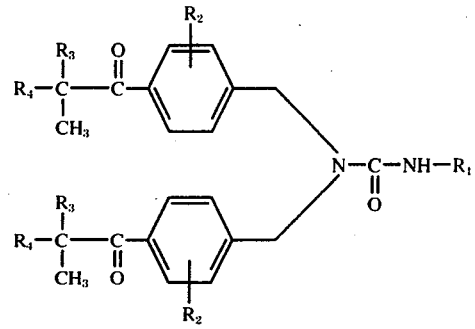

where
$R_1$ represents lower alkyl having 1 to 4 carbon atoms, and
$R_2$ each independently represents hydrogen, halo having an atomic weight of about 19 to 36, and
$R_3$ and $R_4$ each independently represent lower alkyl having 1 to 2 carbon atoms.

2. A compound of the formula

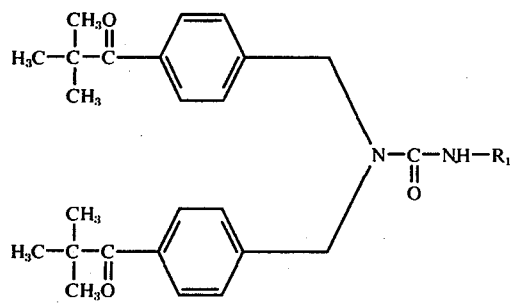

where $R_1$ is as defined in claim 1.

3. A compound of the formula

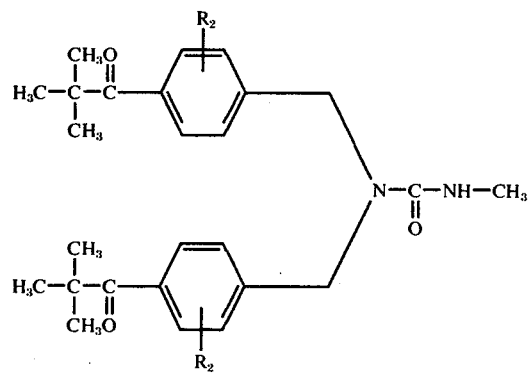

where $R_2$ is as defined in claim 1.

4. The compound of claim 2 which is 1,1-bis(4-pivaloylbenzyl)-3-methyl urea.

5. A composition for lowering lipid levels comprising a hypolipidemically effective amount of the compound of claim 1 and a pharmaceutically acceptable diluent or carrier therefor.

6. A method of treating lipidemia which comprises administering to a mammal in need of said treatment a hypolipidemically effective amount of a compound of claim 1.

* * * * *